United States Patent [19]

Friedman et al.

[11] Patent Number: 5,253,645
[45] Date of Patent: Oct. 19, 1993

[54] METHOD OF PRODUCING AN AUDIBLE ALARM IN A BLOOD PRESSURE AND PULSE OXIMETER MONITOR

[75] Inventors: Bruce A. Friedman, Tampa; Daryl L. Bordon, Temple Terrace; Richard Medero, Tampa, all of Fla.

[73] Assignee: Critikon, Inc., Tampa, Fla.

[21] Appl. No.: 807,537

[22] Filed: Dec. 13, 1991

[51] Int. Cl.⁵ .............................................. A61B 8/14
[52] U.S. Cl. .................................................. 128/633
[58] Field of Search ........................ 128/633, 632, 634

[56]  References Cited
U.S. PATENT DOCUMENTS 4,776,339 10/1988 Schreiber ............................ 128/633
4,889,116 12/1989 Taube .................................. 128/633

*Primary Examiner*—Randall L. Green
*Assistant Examiner*—Gina M. Gualtieri
*Attorney, Agent, or Firm*—Paul A. Coletti

[57] ABSTRACT

A patient monitoring system includes a pulse oximeter sensor and an audible alarm which is not produced when a blood pressure module is taking measurements, but only during that portion of the cycle that affects the pulse oximeter reading. During such measurements, the pulses detected by the oximeter decrease below a threshold $T_{oxim}$. An audible alarm is caused to receive a logic level of zero by an AND gate through the detection of measurements exceeding a minimum pressure $P_{min}$ on the blood pressure module. The audible alarm continues to receive such a logic level until the measurements exceed a threshold $P_{thr}$. After that time, the audible alarm AND gate logic level is reset to one, so as to permit reporting of pulses missing at the oximeter. None of the other alarms, such as the actual SpO₂ reading, are affected by the AND gate. Accordingly, the present invention does not affect the taking of important SpO₂ readings during cuff inflation/deflation and, moreover, only prevents a pulse missing audible alarm from being heard for a short period of time.

10 Claims, 2 Drawing Sheets

METHOD OF PRODUCING AN AUDIBLE ALARM IN A BLOOD PRESSURE AND PULSE OXIMETER MONITOR

BACKGROUND OF THE INVENTION

1. Field of the Invention

The invention relates to a blood pressure and pulse oximeter monitor apparatus that decreases the chance that a spurious loss of pulse signal from the pulse oximeter when the blood pressure cuff is being inflated and deflated will trigger an audible alarm.

2. Description of Related Art

When a pulse oximeter sensor is placed on the same limb as a blood pressure cuff, inflation of the cuff above systolic pressure will eliminate the plethysmographic pulse signal in the finger. See, for example, Pulse Oximetry, Payne and Severinghaus; Springer-Verlag 1986. A pulse oximeter measures the oxygen saturation of arterial blood by comparing the ratio of red light transmission through a pulsatile vascular tissue to infrared light transmission through the same vascular tissue. The absence of either pulsatile signal will cause the pulse oximeter to alarm. The loss of a pulsatile signal can indicate that the sensor is improperly attached, that the patient has no pulse, or some intervention has temporarily eliminated pulsatile flow. Since the loss of the pulsatile signal due to the inflation of the cuff is an artifact and not an indication of a fundamental change in the physiological status of the patient, it is desirable for the oximeter not to alarm in such a case.

Attempts have been made in the prior art to deal with the problem of setting off the pulse oximeter alarm during pressure cuff inflation/deflation. One technique described is in U.S. Pat. No. 4,776,339 entitled INTERLOCK FOR OXYGEN SATURATION MONITOR AESTHESIA APPARATUS discloses a system, including an activatable control means, which is operative to respond to the inflation of the cuff to provide a signal for disabling the oxygen saturation alarm for the time during which the cuff is inflated. Such devices suffer from two major problems. First, they disable more alarms than are necessary. For example, changes in oxygen saturation during the inflation/deflation of the cuff may be physiological and not caused by an artifact, (i.e. the cuff). Second, the normal cuff inflation/deflation cycle time is between 30 and 120 seconds. The pulses detected by the oximeter sensor, however, only fall below a minimal level for a period of time significantly less than that, e.g., 10 seconds. Therefore, it is only necessary to interlock the alarm for a period of roughly 20 seconds rather than interlock against the alarm for a complete cuff inflation/deflation cycle of 30–120 seconds. During the prior art interlock cycle, important alarms may have provided useful alarm information that the system was not capturing or reacting to.

SUMMARY OF THE INVENTION

Briefly described, the present invention comprises a patient monitoring system including an audible alarm which does not spuriously sound as a result of the absence of pulses from an oximeter sensor during a period of time when a blood pressure cuff, placed on the same arm, is inflated/deflated. A conventional blood pressure cuff is placed on an arm of the patient and connected to a plethysmograph which forms part of a blood pressure module. The information from the plethysmograph is decoded by a blood pressure calculator. Another output signal from the blood pressure plethysmograph produces an audible alarm signal, limited by a reset timer which forms a first input to an AND gate connected to the audible alarm.

The output from the pulse oximeter sensor is likewise connected to a plethysmograph. The output from the pulse oximeter plethysmograph is decoded by an $SpO_2$ calculator and the $SpO_2$ value is displayed. The output from the pulse oximeter plethysmograph is also delayed by a timer, and this output forms the second input to the aforementioned AND gate. The output from the timer in the oximeter module is displayed as part of a visual "pulse missing" alarm.

The audible alarm is activated if the alarm signal from the plethysmograph in the oximeter module and the alarm signal from the plethysmograph in the blood pressure module are both at logic level 1. The alarm signal from the blood pressure module drops to a logic level 0 whenever the pulses detected by the plethysmograph exceed a minimum pressure $P_{min}$ but do not exceed a maximum threshold pressure $P_{thr}$. After that point $P_{thr}$, the logic level changes back to "1", and the audible alarm will produce an output, for example, if the pulse signal level measured by the oximeter module does not exceed a threshold $T_{oxim}$. In this manner, the audible alarm does not sound only during the relatively short portion of the cuff inflation/deflation cycle where the cuff creates a loss of the pulsatile signal measured at the oximeter sensor. Moreover, the AND gate logic mechanism only effects the audible alarm. Other oximeter alarms, such as limit alarms on the $SpO_2$ and pulse rate signals will, during the entire period, produce an output if the signal falls outside of predetermined thresholds.

These and other features of the present invention will be more fully understood by reference to the following drawings.

DETAILED DESCRIPTION OF THE INVENTION

During the course of this description, like numbers will be used to indicate like elements according to the different Figures which illustrate the invention.

Figure 1:
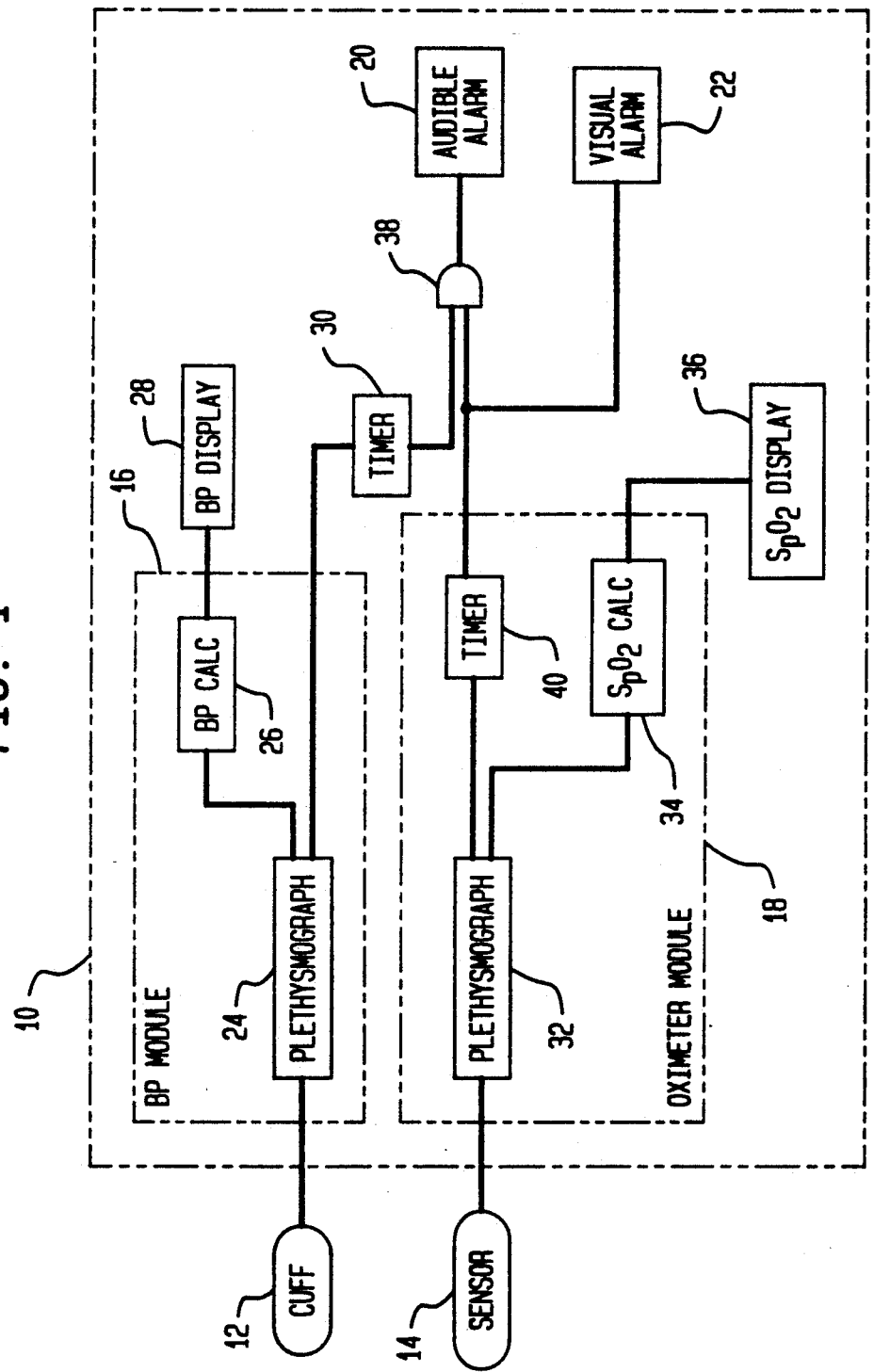
FIG. 1 is a schematic block diagram of the blood pressure and $SpO_2$ monitor according to the preferred embodiment of the present invention.

The preferred embodiment of the invention 10 is illustrated in a schematic block diagram form in FIG. 1. A conventional blood pressure cuff 12 is initially placed on either the right or left arm of the patient. Similarly, only if necessary, for instance, in cases where only one are is available, a conventional oximeter sensor 14 is placed on the finger of the same arm of the patient where the cuff 12 is located. Oximeter sensor 14 monitors the pulse of the patient as well as the oxygen saturation level of the blood. Oxygen saturation is determined by measuring the ratio of visible red light to infrared light that is transmitted through the patient's finger. If a pulse is not detected by the oximeter sensor 14, an audible alarm generally will be sounded absent other informaton provided by the instruments.

The output from the blood pressure cuff 12 provides one input to a conventional plethysmograph 24 in the blood pressure module 16. Plethysmograph 24 can be of a variety of those known in the prior art and such as described in U.S. Pat. Nos. 4,546,775 and 4,638,810 issued to co-inventor Richard Medero and assigned to Critikon, Inc. of Tampa, Fla. A plethysmograph is a term commonly used to describe an instrument that measures the volume of blood that passes through a limb or organ. The output from plethysmograph 24 forms the input to blood pressure calculator 26 which decodes the output and displays it as part of blood pressure display 28. Another output from plethysmograph 24 forms an input to timer 30 which enables the timer 30 when the signal changes from logic level 1 to logic level 0. The timer 30 input signal from plethysmograph 24 and timer 30 output to audible alarm 20 are set to logic level 0 when the measured oscillations in the cuff 12 exceed the minimum threshold $P_{min}$. Timer 30 input and output are reset to level 1 when the oscillations exceed the threshold $P_{thr}$ as shown in FIG. 2B. The output of timer 30 automatically resets to logic level 1 if the level $P_{thr}$ is not reached within twenty seconds after reaching $P_{min}$. The output from timer 30 forms a first input to AND gate 38. The output from AND gate 38 forms the input to audible alarm 20.

The output from oximeter sensor 14 forms the input to the oximeter plethysmograph 32 of oximeter module 18. Oximeter plethysmograph 32 can be a conventional plethysmograph such as described in U.S. Pat. No. 4,807,631 issued to Hersh, et al. and assigned to Critikon, Inc., Tampa, Fla. The output from oximeter plethysmograph 32 forms an input to $SpO_2$ calculator 34 which decodes the output from plethysmograph 32 and provides an input to the continuous $SpO_2$ display 36. The $SpO_2$ display 36 provides a continuous visual output of the oxygen saturation level detected by oximeter sensor 14 and is not controlled at any time by the output of the blood pressure module 16. The output from the oximeter plethysmograph 32 forms an input to timer 40 whose output provides a second logic level input to AND gate 38. Internal timer 40 adds a ten second delay to the output from oximeter plethysmograph 32. If the pulse strength measurements from sensor 14 remain below minimum threshold $T_{oxim}$ for ten seconds, visual alarm 22 provides a visual indication. The state of the visual alarm is not affected by the status of the alarm signal available from AND gate 38.

Figure 2A:
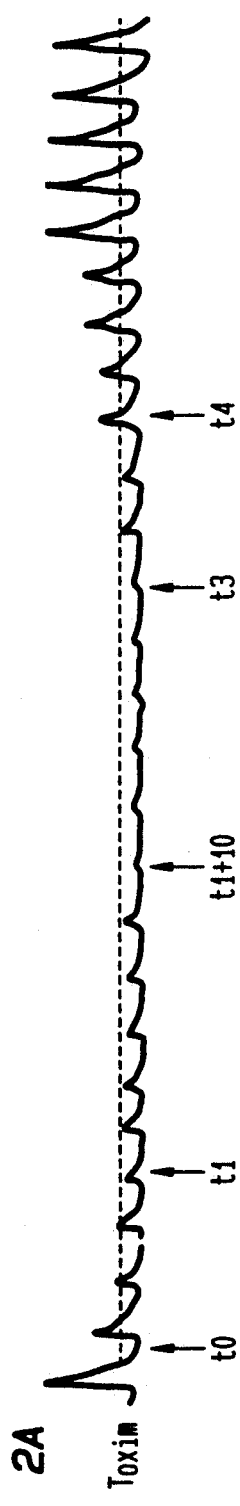
FIGS. 2A-2C illustrate, respectively, in graphic form, the relationship between the plethysmographic pulses measured at the pulse oximeter, oscillations in blood pressure monitored at the cuff including the period during which the audible alarm does not sound, and the pressure in the cuff also indicating the span of time during which prior art alarms were interlocked, and therefore, disabled.
Figure 2B:
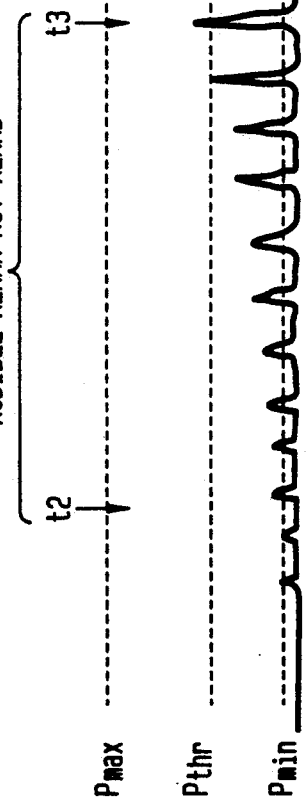
Figure 2C:
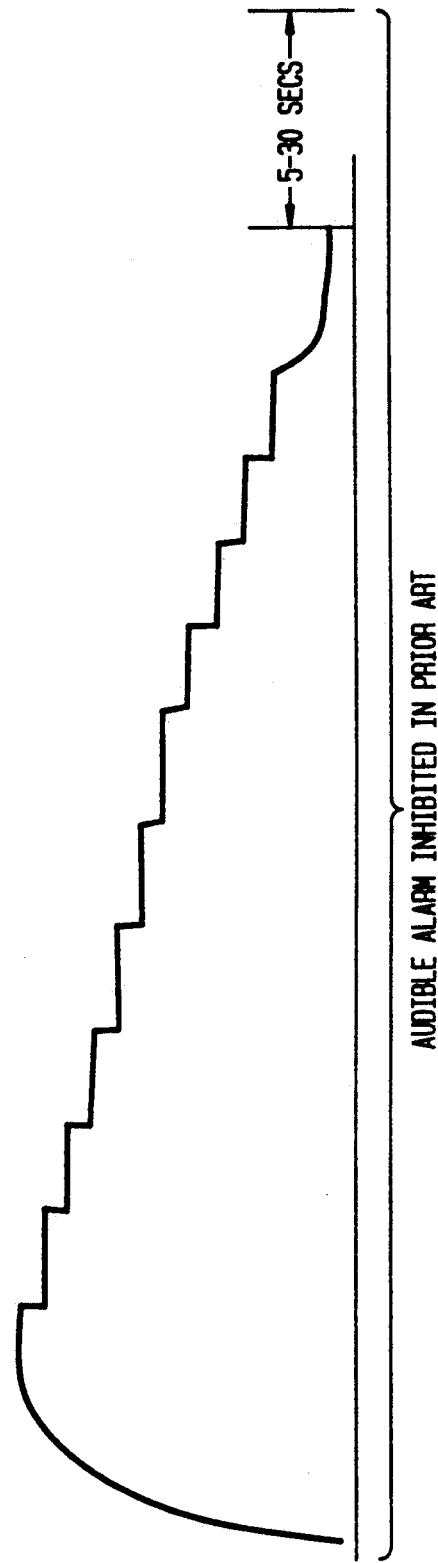

The operation of the preferred embodiment of the invention 10 illustrated in FIG. 1 is shown in graphic form in FIGS. 2A-2C. The top trace or graph 2A indicates the plethysmographic pulses created by the oximeter sensor 14. Graph 2B illustrates the relative pressure cuff oscillations detected at cuff 12. The period between times t2 and t3, during which the audible alarm is not heard is superimposed upon graph 2B. Lastly, graph 2C illustrates the relative cuff pressure. Superimposed along the bottom of graph 2C is the prior art alarm inhibit span which is indicated. This time span is substantially longer than the time during which the audible alarm is not heard in the present invention 10 as shown in graph 2B as a result of the logic level 0 input coming from AND gate 38.

Initially, at all times prior to t0 and t2, the pressure in the cuff 12 is increased as indicated in graph 2C. Increasing pressure in the cuff 12 occludes the artery in the arm and causes the plethysmographic pulses detected by oximeter sensor 14 to decrease as illustrated in the upper graph 2A. Deflation of the cuff 12 according to standard known techniques from its peak point of inflation will cause cuff oscillations to be detected as shown in graph 2B. The onset of the detection of these pulses is generally an indication of the systolic pressure of the patient. Prior to points t0 and t2, the output from the blood pressure plethysmograph produces a signal at logic level 1 which passes through timer 30 and enables AND gate 38 so as to pass through an alarm signal from oximeter sensor 14 if the pulse level detected by oximeter sensor 14 falls below the threshold $T_{oxim}$. However, since it is known that occluding the patient's artery will automatically cut off the patient's pulse measured by sensor 14, it may be necessary to cause the audible alarm 20 not to be sounded during that selected period of time in which this artifact is known to exist.

In summary, the audible alarm 20 is initially caused to be heard if the pulse missing alarm signal from the $SpO_2$ module 18 and the alarm inhibit signal from the blood pressure module 16 are both set at logic level 1. The alarm signal from oximeter module 18 is at logic level 1 when the $SpO_2$ module 18 has not detected a valid pulse for a period of time $T_2 =$ ten seconds as measured by internal timer 40.

The audible alarm signal for loss of pulsatile signal is not heard at time t2 when the cuff pulse oscillations exceed a predetermined minimum value $P_{min}$, as shown in graph 2B. When the measured pulse oscillation in the plethysmograph 24 exceeds $P_{min}$, the output from blood pressure module 16 to timer 30 and, ultimately to AND gate 38 is set to logic level 0. This output signal remains at logic level 0 until the measured oscillations exceed threshold $P_{thr}$ at time t3. Since the signal which reaches audible alarm 20 is at logic level 0 during the period from t2 to t3, the audible alarm 20 is masked, and not heard, as illustrated by the bracket in graph 2B. After point t3, the input signal to AND gate 38 is reset to logic level 1, thereby enabling the audible alarm 20. The input signal to AND gate 38 is also reset to logic level 1 by the blood pressure reset timer 30 if the threshold oscillation pressure $P_{thr}$ is not reached within a period of time $T_1 = 20$ seconds.

During the time when an audible alarm is not heard, that is t2 through t3, the output from the oximeter module 18 received at AND gate 38 is ineffective to cause audible alarm 20 to be heard. However, visual alarm 22 is activated at time t1+10 seconds as indicated on graph 2A. Time t1 is the point at which the pulse detected by oximeter sensor 14 falls below $T_{oxim}$. As can be realized from these FIGS. 2A-2C, the activation of visual alarm 22 is independent of the status of the alarm signal received from AND gate 38.

If the pulse plethysmograph signal after the interval t3 is less than the threshold $T_{oxim}$, then the AND gate 38 will activate the alarm 20. On the other hand, if the pulse plethysmographic signal exceeds $T_{oxim}$, then the AND gate 38 has a logic level 0 and the alarm 20 will not be sounded. As shown in graph 2A, the pulse plethysmographic sensor signal is less than $T_{oxim}$ during the interval t3 through t4 and, accordingly, the audible alarm 20 would be enabled and sounded. However, after point t4, the pulse plethysmographic signal exceeds $T_{oxim}$ and, therefore, the alarm 20 is not sounded.

Initially, the threshold pressure $P_{thr}$ is set to a nominal value. After the first determination, it is adaptively set to 60% of $P_{max}$ from the previous determination. $P_{max}$ typically corresponds to the mean blood pressure of the patient and may be captured for future calculations. Similarly, the point at which the blood pressure oscillations illustrated in FIG. 2B drop below the minimum value $P_{min}$ corresponds roughly to the diastolic pressure of the patient.

The logic states for the preferred embodiment of the invention 10 illustrated in FIG. 1 and graphically shown in FIGS. 2A-2C are summarized in the logic table set forth below.

LOGIC TABLE FOR ALARM 20

| Time | First Gate Input Logic Level | Second Gate Input Logic Level | System Status |
|---|---|---|---|
| t0 | 1 | 0 | Cuff 12 inflation begins. |
| t1 | 1 | 0 | Oximeter plethysmograph signal drops below $T_{oxim}$. |
| t2 | 0 | 0 | Cuff oscillations reach $P_{min}$; audible alarm period begins wherein the signal is not heard. |
| t1 + 10 | 0 | 1 | Oximeter alarm activated; visual alarm 22 on; audible alarm 20 continues to be not heard. |
| t3 | 1 | 1 | Cuff oscillations reach $P_{thr}$, audible alarm 20 sounds. |
| t4 | 1 | 0 | Oximeter plethysmograph signal exceeds $T_{oxim}$; audible and visual alarms 20 and 22 off. |

Some of the advantages of the present invention are apparent from graphs 2A-2C and the foregoing description. FIG. 2C includes a portion indicative of the audible alarm interlock span typical of the prior art. The timespan is conspicuously longer than the timespan according to the preferred embodiment 10 of the present invention in which an alarm signal is not heard, as illustrated in FIG. 2B. Accordingly, the present invention 10 is more sensitive to the vital signs of the patient because its "pulse missing" signal audible alarm is not heard for a shorter period of time. Moreover, the present invention comprehends only causing the audible alarm associated with a missing pulse signal from the oximeter sensor 14 to not be heard. It does not inhibit any other alarms such as visual alarm 22 or blood pressure and SpO2 displays 28 and 36, respectively.

The invention disclosed above was achieved with items of discrete conventional hardware but it is possible for much of the logic to be accomplished with integrated semiconductor circuits driven by the appropriate software instructions.

While the invention has been described with reference to the preferred embodiment thereof, it will be appreciated by those of ordinary skill in the art that various modifications and changes may be made to the invention without departing from the spirit and scope thereof.

We claim:

1. A method for producing an audible alarm in a patient monitoring system including a blood pressure module having a cuff placed on a limb of a patient and a pulse oximeter placed on the limb of the patient, comprising the steps of:

using said cuff to measure peak oscillation amplitudes of the blood pressure of said patient over a blood pressure measurement cycle and to produce a first output which represents a first logical state;

using said pulse oximeter to measure an oxygen saturation (SpO2) level of said patient and to produce a second logical state;

inputting said first and second logical states into a gate producing an output from said gate, said output capable of enabling an audible alarm; and masking said second logical state as input for enabling said audible alarm in said gate whenever said peak oscillation amplitudes fall in a range between a minimum level $P_{min}$ and a threshold level $P_{thr}$, wherein during said masking of said second logical state, said audible alarm rejects a spurious oxygen saturation level alarm and said masking does not occur during at least a portion of said blood pressure measurement cycle.

2. The method of claim 1 further comprising the step of:

causing said audible alarm to be produced when said blood pressure peak oscillation amplitudes do not reach $P_{thr}$ within a fixed period of time $T_1$ after $P_{min}$ is reached.

3. The method of claim 2 further comprising the step of:

measuring the pulse of the patient with said pulse oximeter and producing an alarm output when said pulse oximeter has not detected a valid pulse within a predetermined period of time $T_2$.

4. The method of claim 3 further comprising the step of:

initially setting $P_{thr}$ at a nominal value and thereafter determining a maximum peak oscillation amplitude $P_{max}$ and subsequently resetting $P_{thr}$ to be predetermined percentage $P_x$ of $P_{max}$.

5. The method of claim 4 further comprising the step of:

visually displaying peak oscillation amplitudes.

6. The method of claim 5 further comprising the step of:

continuously visually displaying said SpO2 level.

7. The method of claim 6 further comprising the step of:

producing a visual alarm indicating that the pulse of said patient has fallen below a level $T_{oxim}$, when no valid pulse has been detected for said period of time $T_2$.

8. The method of claim 2 wherein $T_1$ is approximately 20 seconds.

9. The method of claim 3 wherein $T_2$ is approximately 10 seconds.

10. The method of claim 4 wherein said predetermined percentage $P_x$ is approximately 60% of $P_{max}$.

* * * * *